(12) United States Patent
Tatenuma et al.

(10) Patent No.: US 9,236,153 B2
(45) Date of Patent: Jan. 12, 2016

(54) METHOD OF RECOVERING ENRICHED RADIOACTIVE TECHNETIUM AND SYSTEM THEREFOR

(75) Inventors: Katsuyoshi Tatenuma, Mito (JP); Tomomi Ueda, Mito (JP); Kiyoko Kurosawa, Mito (JP); Koji Ishikawa, Mito (JP); Atsushi Tanaka, Mito (JP); Tsuneyuki Noguchi, Mito (JP); Yasushi Arano, Chiba (JP)

(73) Assignee: KAKEN CO., LTD., Mito-Shi, Ibaraki (JP)

( * ) Notice: Subject to any disclaimer, the term of this patent is extended or adjusted under 35 U.S.C. 154(b) by 1033 days.

(21) Appl. No.: 13/378,819

(22) PCT Filed: Jul. 3, 2009

(86) PCT No.: PCT/JP2009/062570
§ 371 (c)(1),
(2), (4) Date: Dec. 16, 2011

(87) PCT Pub. No.: WO2010/146722
PCT Pub. Date: Dec. 23, 2010

(65) Prior Publication Data
US 2012/0090431 A1 Apr. 19, 2012

(30) Foreign Application Priority Data

Jun. 19, 2009 (JP) ................................ 2009-146555

(51) Int. Cl.
| C01G 49/00 | (2006.01) |
| G21G 1/00 | (2006.01) |
| A61K 51/12 | (2006.01) |
| G21C 19/42 | (2006.01) |
| G21C 19/46 | (2006.01) |

(52) U.S. Cl.
CPC ............ *G21G 1/001* (2013.01); *A61K 51/1282* (2013.01); *G21C 19/42* (2013.01); *G21C 19/46* (2013.01); *G21G 2001/0042* (2013.01); *Y02W 30/883* (2015.05)

(58) Field of Classification Search
CPC ........ B01D 59/25; B01D 59/11; C01G 49/00; C01G 57/00; C22B 34/00
USPC ................................ 423/2, 22, 249
See application file for complete search history.

(56) References Cited

U.S. PATENT DOCUMENTS

| 4,683,123 A | * | 7/1987 | Knapp et al. ....................... 423/2 |
| 5,583,259 A | | 12/1996 | Brown | |
| 5,774,782 A | * | 6/1998 | Mirzadeh et al. ................. 423/2 |

FOREIGN PATENT DOCUMENTS

| JP | 57-118031 | 7/1982 |
| JP | 64-23199 | 1/1989 |
| JP | 1-215727 | 8/1989 |
| JP | 2-054732 | 2/1990 |
| JP | 7-508994 | 10/1995 |
| JP | 8-309182 | 11/1996 |
| JP | 09-122636 | 5/1997 |
| JP | 9-328495 | 12/1997 |
| JP | 2001-112624 | 4/2001 |
| JP | 2004-150977 | 5/2004 |
| JP | 2004-283163 | 10/2004 |
| JP | 2008-102078 | 5/2008 |
| JP | 2008-193964 | 8/2008 |

OTHER PUBLICATIONS

International Search Report with Written Opinion for International Application PCT/JP2009/062570 mailed Aug. 25, 2009.
M. Kimura, et al., "Kasseitan o Mochiiru Suichu no Molybdenum (VI) no Bunri Noshukuho", Bunseki Kagaku, vol. 38, 1989, pp. 529-534.

* cited by examiner

*Primary Examiner* — Michael G Hartley
*Assistant Examiner* — Jagadishwar Samala
(74) *Attorney, Agent, or Firm* — Brundidge & Stanger, P.C.

(57) ABSTRACT

To use $^{99m}Tc$ as a raw material for a radioactive medicine, a very small amount of $^{99m}Tc$ in the high concentration $Mo(^{99}Mo)$ solution is purified and recovered with high yield without contamination of $^{99}Mo$. $^{99m}Tc$ with high purity is recovered by forming a high concentration $Mo(^{99}Mo)$ solution which contains radionuclides $^{99}Mo$ which is the parent nuclide of $^{99m}Tc$ used for the radioactive medicine and the raw material for its labeled compound, forming a high concentration $Mo(^{99}Mo)$ solution which contains radionuclides $^{99}Mo$ and $^{99m}Tc$ by generating $^{99m}Tc$ to a radioactive-equilibrium state, getting $^{99m}Tc$ in the high concentration $Mo(^{99}Mo)$ solution adsorbed to activated carbon selectively by feeding the solution to an adsorption column which has activated carbon, and undergoing desorption and purification treatment of $^{99m}Tc$ with a desorbent from the activated carbon to which $^{99m}Tc$ is adsorbed.

8 Claims, 9 Drawing Sheets

WASHING OF HIGH-CONCENTRATION Mo($^{99}$Mo) SOLUTION WHICH REMAINES INSIDE AC PORE: REMOVAL OF Mo($^{99}$Mo)
[METHOD OF Mo WASHOUT] WATER WASHING + ALKALINE WATER & AIR-BLOW & HEATING UNDER PRESSURIZATION

THERE IS NO MOVEMENT OF Tc ADSORPTION ZONE, EVEN IN OPERATION OF Mo WASHOUT

FIG. 8

YIELD OF $^{99m}$Tc BY SEPAREATION OF ALUMINA COLUMN

| No. | SAMPLE NAME | $^{99m}$Tc RADIO-ACTIVITY (Bq) | $^{99m}$Tc YIELD (%) | |
|---|---|---|---|---|
| ⑪ | BEFORE FEEDING WATER TO ALUMINA COLUMN | 2.01E+04 | | |
| ⑫ | AFTER FEEDING WATER TO ALUMINA COLUMN | 2.01E+04 | 100 | ← ALUMINA COLUMN; 100% OF Tc PURIFICATION AND RECOVERY RATE |

US 9,236,153 B2

METHOD OF RECOVERING ENRICHED RADIOACTIVE TECHNETIUM AND SYSTEM THEREFOR

BACKGROUND OF THE INVENTION

The present invention relates to a method of recovering enriched radioactive technetium ($^{99m}$Tc) as a radioactive medicine and a raw material for its labeled-compound raw material, and a system therefor.

Tc (technetium) is the transition metal of the atomic number 43 which is situated on the 7th family, the 5th period. Out of the isotopes, $^{99m}$Tc radiates only γ-ray with the short half-life (6 hours) which suited a diagnostic imaging and the weak energy (140 keV) which suited an external counting. Moreover, $^{99m}$Tc can be generated by the generator (the $^{99}$Mo-$^{99m}$Tc generator) which utilizes a radiation equilibrium with $^{99}$Mo and it is used for the nuclear medicine diagnostic imaging. $^{99m}$Tc is generally used in the way of obtaining it from $^{99}$Mo (with the half-life of 66 hours) which is the parent nuclide of $^{99m}$Tc with a short half-life. Methods for obtaining $^{99}$Mo include the Fission method (the nuclear fission method) in which $^{99}$Mo with very high specific radioactivity is first generated by the method of uranium nuclear fission, and then separated. In this case, a method of obtaining $^{99m}$Tc by a milking operation in which the $^{99m}$Tc is eluted with a physiological saline using alumina as a $^{99}$Mo adsorbent, is used as the actual manufacturing technology. On the other hand, there is another method of generating $^{99}$Mo using the (n,γ) reaction of the $^{98}$Mo isotope which is contained in $^{99}$Mo, instead of using uranium as the raw material for obtaining $^{99}$Mo. In comparison with the Fission method, this (n,γ) method enables a specific radioactivity of $^{99}$Mo to be lowered to about 1/10,000. Therefore, for the practical application of the (n,γ) method, a small amount of $^{99}$Tc must be separated, purified and recovered as the daughter nuclide generated from a small amount of $^{99}$Mo which is contained in a large amount of Mo. So far, a sol-gel method, MEK method, or a sublimation method are known as the investigated and practically useful (n,γ) method. The inventors of this application have separately proposed PZC method as the (n,γ) method.

JP 2008-102078 A discloses the method and the equipment, in which radioactive molybdenum $^{99}$Mo as the parent nuclide of technetium is generated by the $^{98}$Mo(n,γ) reaction in a nuclear reactor.

JP 08-309182 A discloses Mo adsorbent for the $^{99}$Mo-$^{99m}$Tc generator. And, it is described that this Mo adsorbent is formed by the zirconium-based inorganic polymer which has a high Mo adsorption ability and a high Tc elution performance. This Mo adsorbent is insoluble in water, adsorbs only Mo (including $^{99}$Mo) from a water solution which contains Mo (including $^{99}$Mo), and elutes $^{99m}$Tc generated from the radioisotope of $^{99}$Mo. Furthermore, this patent literature discloses that a gel of ZrO$^{99}$MoO$_4$.xH$_2$O is synthesized by reacting Na$_2$Mo($^{99}$Mo)O$_4$ obtained by dissolution of Mo($^{99}$MoO$_3$) in the (n, γ) method with ZrOCl$_2$ or ZrO(NO$_3$)$_2$, dried, pulverized and packed into a column, and that $^{99m}$Tc can be eluted from the packed column by a milking operation.

JP 02-54732 A discloses that technetium is eluted from activated carbon which adsorbs and separates technetium from a solution which contains technetium, such as a high radioactive-effluent, or a spent nuclear fuel solution which is generated by reprocessing of a spent nuclear fuel. Technetium in this case is not directed to $^{99m}$Tc (technetium-$^{99}$m) with the short half-life for the nuclear medicine diagnostic imaging, but to $^{99}$Tc with a very long half-life (technetium 99: the half-life of 21 ten thousand years), which causes a problem of remaining in the nuclear waste.

{Patent Literature 1} Japanese Patent Application Laid-Open No. 2008-102027

{Patent Literature 2} Japanese Patent Application Laid-Open Hei No. 08-309182

{Patent Literature 3} Japanese Patent Application Laid-Open Hei No. 02-54732

SUMMARY OF INVENTION

The conventional method has several problems such as a low performance stability, an operational complexity, an occurrence of radiation damage or a difficulty peculiar to the (n, γ) method in operation of a large amount of Mo, which does not reach the establishment of the practical technique which is equal to the Fission method.

To apply $^{99m}$Tc Mo generated as the daughter nuclide of $^{99}$Mo by the (n, γ) method to the raw material for the radioactive medicine, the purification and recovery of a very small amount of $^{99m}$Tc in high concentration Mo which contains the radioactive molybdenum ($^{99}$Mo) must be made with high yield without contamination of $^{99}$Mo. Therefore, the (n,γ) method demands a use of the adsorbent which adsorbs a very small amount of $^{99m}$Tc in high concentration Mo which contains a very small amount of $^{99}$Mo, and further a recovery processing for elution and recovery with high yield of $^{99m}$Tc which is adsorbed to the adsorbent.

As for the conventional technology, $^{99}$Tc is eluted from a solid-like or gelatinous adsorbent of Mo($^{99}$Mo) to which Mo (including $^{99}$Mo) is adsorbed. Aforementioned JP 02-54732 A discloses that technetium is separated by adsorption to activated carbon, which indicates that the activated carbon has a performance of adsorbing and separating technetium. However, the invention of JP 02-54732 A is directed to $^{99}$Tc (Technetium) of the long half-life which is contained in the high radioactive-effluent of the strong nitric acid acidity which is generated by the reprocessing of the spent nuclear fuel, and there is no disclosure about the method of purifying and recovering a very small amount of 99mTc when producing a raw material for a radioactive medicine.

The present invention is devised to use Tc as a raw material for a radioactive medicine in view of the above point, and has the purpose of providing a method and a system of purifying and recovering a very small amount of $^{99m}$Tc with high yield (95% and more) without contamination of Mo ($^{99}$Mo) from a large amount of Mo which contains a small amount of $^{99}$Mo, together with reduction of waste fluid and wastes, using radioactive Mo generated by the (n, γ) method.

According to the study of the present invention, it is found that $^{99m}$Tc enriched to the required concentration as the radioactive medicine and the raw material for its labeled compound can be obtained by forming the high concentration Na$_2$Mo($^{99}$Mo)O$_4$ solution of neutral pH in which a large amount of Mo($^{99}$Mo)O$_3$ is dissolved with alkaline (NaOH), getting a small amount of $^{99m}$Tc generated in the high concentration Mo solution adsorbed to activated carbon selectively, making $^{99m}$Tc stay behind the activated carbon by desorption of the Mo (including $^{99}$Mo) remaining in its holes from it, and recovering a trace of the remained $^{99m}$Tc.

The present invention provides a method of highly enriching, and eluting, purifying and recovering $^{99m}$Tc as a raw material for a radioactive medicine, characterized by the steps of:

forming a high concentration Mo solution which contains radioactive molybdenum ($^{99}$Mo) as the parent nuclide of $^{99m}$Tc as a radioactive medicine and a raw material for its labeled compound;

feeding the Mo($^{99}$Mo) solution to an adsorption column which has an activated carbon from the high concentration Mo solution which contains radionuclides $^{99}$Mo and $^{99m}$Tc which is generated as the daughter nuclide of $^{99}$Mo, getting $^{99m}$Tc in the high concentration Mo($^{99}$Mo) adsorbed to the activated carbon selectively, then getting Mo($^{99}$Mo) remaining in holes of the activated carbon desorbed with a desorbent, undergoing desorption treatment of a small amount of $^{99m}$Tc which adsorbs to and stays behind the activated carbon with a desorbent of $^{99m}$Tc from the activated carbon, and recovering $^{99m}$Tc;

making secondary purification to remove Mo($^{99}$Mo) remaining a little in the recovered $^{99m}$Tc by a alumina column method; and recirculating and recovering the high concentration Na$_2$Mo($^{99}$Mo)O$_4$ solution after desorption treatment of $^{99m}$Tc to recover $^{99m}$Tc again after 24 hours when $^{99m}$Tc is re-formed.

The present invention also provides a method of highly enriching, and eluting, purifying and recovering $^{99m}$Tc directly from the high concentration Na$_2$Mo($^{99}$Mo)O$_4$ solution of neutral pH which is formed by dissolving Mo($^{99}$Mo)O$_3$ containing radionuclide $^{99}$Mo with an alkaline solution.

The present invention also provides a method of highly enriching, and eluting, purifying and recovering $^{99m}$Tc, characterized by the steps of: removing Mo($^{99}$Mo) remaining in activated carbon by washing the activated carbon adsorbing $^{99m}$Tc with dilute alkaline solution; and then further undergoing desorption treatment of $^{99m}$Tc with a high concentration alkaline solution, when recovering $^{99m}$Tc by the desorption treatment from the activated carbon adsorbing $^{99m}$Tc.

The present invention also provides a method of highly enriching, and eluting, purifying and recovering $^{99m}$Tc, characterized by the steps of eluting and recovering $^{99m}$Tc by treating the activated carbon with the NaOH solution of 0.05 mole (M) and more at 100° C. and more and at 5 atm and more.

The present invention also provides a method of highly enriching, and eluting, purifying and recovering $^{99m}$Tc, characterized by the step of undergoing electrochemical treatment of the activated carbon adsorbing $^{99m}$Tc by using the activated carbon as a cathode, when recovering $^{99m}$Tc by the desorption treatment of $^{99m}$Tc.

The present invention also provides a method of highly enriching, and eluting, purifying and recovering $^{99m}$Tc, characterized by the step of undergoing reduction treatment of the activated carbon adsorbing $^{99m}$Tc by a reductant, when recovering $^{99m}$Tc by the desorption treatment of $^{99m}$Tc.

The present invention also provides a method of highly enriching, and eluting, purifying and recovering $^{99m}$Tc, characterized by the step of recovering $^{99m}$Tc in combination of the treatment with the high concentration alkaline, the electrochemical treatment and the reduction treatment with the reductant. And, in this case, the step can combine the secondary purification to remove Mo ($^{99}$Mo) remaining a little in the recovered $^{99m}$Tc by the alumina column method, The present invention provides a system of highly enriching, and eluting, purifying and recovering $^{99m}$Tc as a raw material for a radioactive medicine, comprising the steps of:

forming a high-concentration Mo solution of neutral pH which contains $^{99}$Mo as the parent nuclide of $^{99m}$Tc used for a radioactive medicine and its raw material;

preparing a high concentration Mo($^{99}$Mo) solution which contains $^{99m}$Tc by generating $^{99m}$Tc to a radiation-equilibrium state in this high concentration Mo($^{99}$Mo) solution;

getting a small amount of $^{99m}$Tc in the high concentration Mo($^{99}$Mo) solution adsorbed to the activated carbon selectively by feeding the formed high-concentration Mo($^{99}$Mo) solution to an adsorption column which has activated carbon, and washing and removing Mo($^{99}$Mo) remaining in said activated carbon to which $^{99m}$Tc is adsorbed, with a Mo desorbent;

adsorbing, desorbing, and recovering and purifying $^{99m}$Tc by undergoing desorption treatment of $^{99m}$Tc with a $^{99m}$Tc desorbent from the activated carbon to which $^{99m}$Tc is adsorbed, after washing and removing Mo($^{99}$Mo) remaining in the activated carbon to which $^{99m}$Tc is adsorbed, with a Mo adsorbent;

making secondary purification to remove Mo($^{99}$Mo) remaining a little in the recovered $^{99m}$Tc by the alumina column method; and recirculating and recovering the high-concentration Mo($^{99}$Mo) solution by circulating and recovering to reuse the high concentration Mo($^{99}$Mo) solution after the desorption treatment of $^{99m}$Tc, generating $^{99m}$Tc to a radiation-equilibrium condition, and re-forming high concentration Mo solution containing radionuclides $^{99}$Mo and $^{99m}$Tc.

The present invention provides a system of highly enriching, and eluting, purifying and recovering $^{99m}$Tc as a raw material for a radioactive medicine, comprising the steps of:

forming a high concentration Mo solution of neutral pH by dissolving MoO$_3$ which contains $^{99}$Mo irradiated with neutron in a nuclear reactor, with an alkaline solution, as a method for forming a high-concentration Mo solution which contains $^{99}$Mo as the parent nuclide of $^{99m}$Tc used as a radioactive medicine and its raw material;

forming the high concentration Mo solution which contains radionuclides $^{99}$Mo and $^{99m}$Tc which is genarated to a radiation-equilibrium state so as to be the daughter nuclide of 99Mo, in the high concentration Mo($^{99}$Mo) solution;

getting $^{99m}$Tc in the high-concentration Mo($^{99}$Mo) solution adsorbed to the activated carbon selectively by feeding the high-concentration Mo($^{99}$Mo) solution which contains $^{99m}$Tc generated to a radiation-equilibrium, to an adsorption column which has said activated carbon, and desorbing the Mo($^{99}$Mo) by washing the Mo($^{99}$Mo) remaining at the activated carbon with a Mo desorbent;

desorbing, and purifying and recovering $^{99m}$Tc to recover $^{99m}$Tc by undergoing desorption treatment of $^{99m}$Tc with a $^{99m}$Tc desorbent from the activated carbon to which $^{99m}$Tc is adsorbed after the desorption treatment of Mo($^{99}$Mo);

circulating and recovering the high-concentration Mo($^{99}$Mo) by circulating and recovering to reuse the high concentration Mo($^{99}$Mo) solution after the desorption and recovery treatment of $^{99m}$Tc, generating $^{99m}$Tc to a radiation-equilibrium condition and re-forming the high-concentration Mo solution containing radionuclides $^{99}$Mo and $^{99m}$Tc; and making secondary purification to remove Mo($^{99}$Mo) remaining a little in the recovered $^{99m}$Tc by the alumina column method.

The present invention employs the method of preparing Na$_2$Mo($^{99}$Mo)O$_4$ solution condition in which $^{99m}$Tc of the radiation-equilibrium state is generated from $^{99}$Mo and is mixed by leaving the high concentration Mo (including radioactive $^{99}$Mo) solution formed in the above mentioned method for about 24 hours, and feeding the Na$_2$Mo($^{99}$Mo)O$_4$ solution containing $^{99m}$Tc to the activated carbon. According to the present invention, only a small amount of $^{99m}$Tc in the high concentration Mo($^{99}$Mo) solution is selectively adsorbed to activated carbon and $^{99m}$Tc is desorbed after removing Mo($^{99}$Mo) which remains in the activated carbon, which results in a sufficient performance of the activated carbon for recovery of $^{99m}$Tc, and a high yield (of 95% and more) in the purification and recovery of a small amount of $^{99m}$Tc in the high concentration Mo solution. The present invention can also purify and recover $^{99m}$Tc with high purity without contamination of $^{99}$Mo by feeding the recovered solution of $^{99m}$Tc to the alumina column, although Mo($^{99}$Mo) remaining a little in activated carbon is eluviated simultaneously with $^{99m}$Tc in the adsorption treatment of $^{99m}$Tc.

BRIEF DESCRIPTION OF DRAWINGS

FIG. 8 shows the $^{99m}$Tc yield in alumina column separation.

DESCRIPTION OF THE PREFERRED EMBODIMENTS

The following will explain preferred modes of implementing the present invention referring to attached drawings. Hereinafter, $^{99m}$Tc and radionuclide $^{99}$Mo are sometimes described as technetium or merely Tc and merely $^{99}$Mo, respectively.

Figure 1:
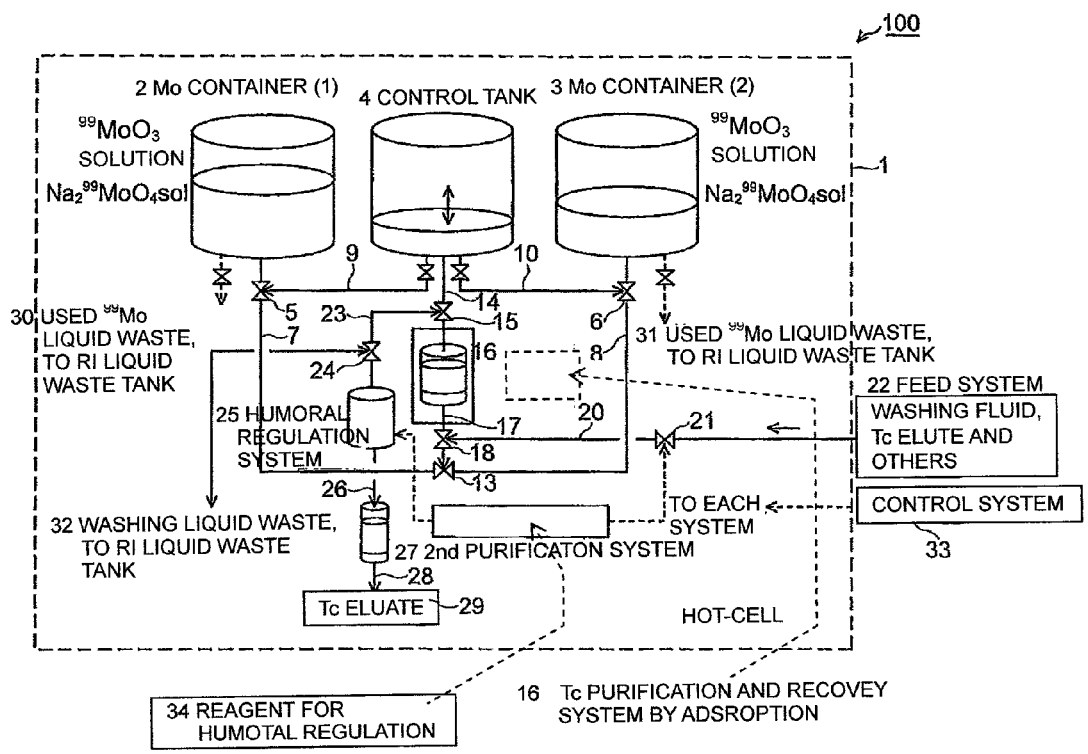
FIG. 1 illustrates the system configuration of one embodiment of the present invention.

FIG. 1 illustrates the system concept for highly enriching, and eluting and recovering $^{99m}$TC (hereinafter, it is called a main system, and the method implemented by this system is called a main system way) which is one embodiment of the present invention. The system for highly enriching, and eluting and recovering $^{99m}$TC can be equipped with the purification and separation procedure.

In FIG. 1, main system 100 is installed in a hot-cell 1 which shields radiation emitted from $^{99}$Mo and $^{99m}$Tc. The main system 100 is equipped with Mo container (1) 2, Mo container (2) 3 and a control tank 4. A plurality of Mo containers may be equipped. The Na$_2$$^{99}$MoO$_4$ solution, which is formed by dissolving MoO$_3$ which contains $^{99}$Mo generated by neutron irradiation in a nuclear reactor with an alkaline (NaOH) solution, is supplied to Mo container (1) 2 and Mo container (2) 3. That is, the Mo solution which contains radionuclide $^{99}$Mo as the raw material for the radioactive-medicine is supplied to Mo container (1) 2 and Mo container (2) 3. When $^{99}$MoO$_3$ is dissolved with an alkaline solution, the Na$_2$$^{99}$MoO$_4$ solution of neutral pH is formed as shown in the figure.

Figure 3:
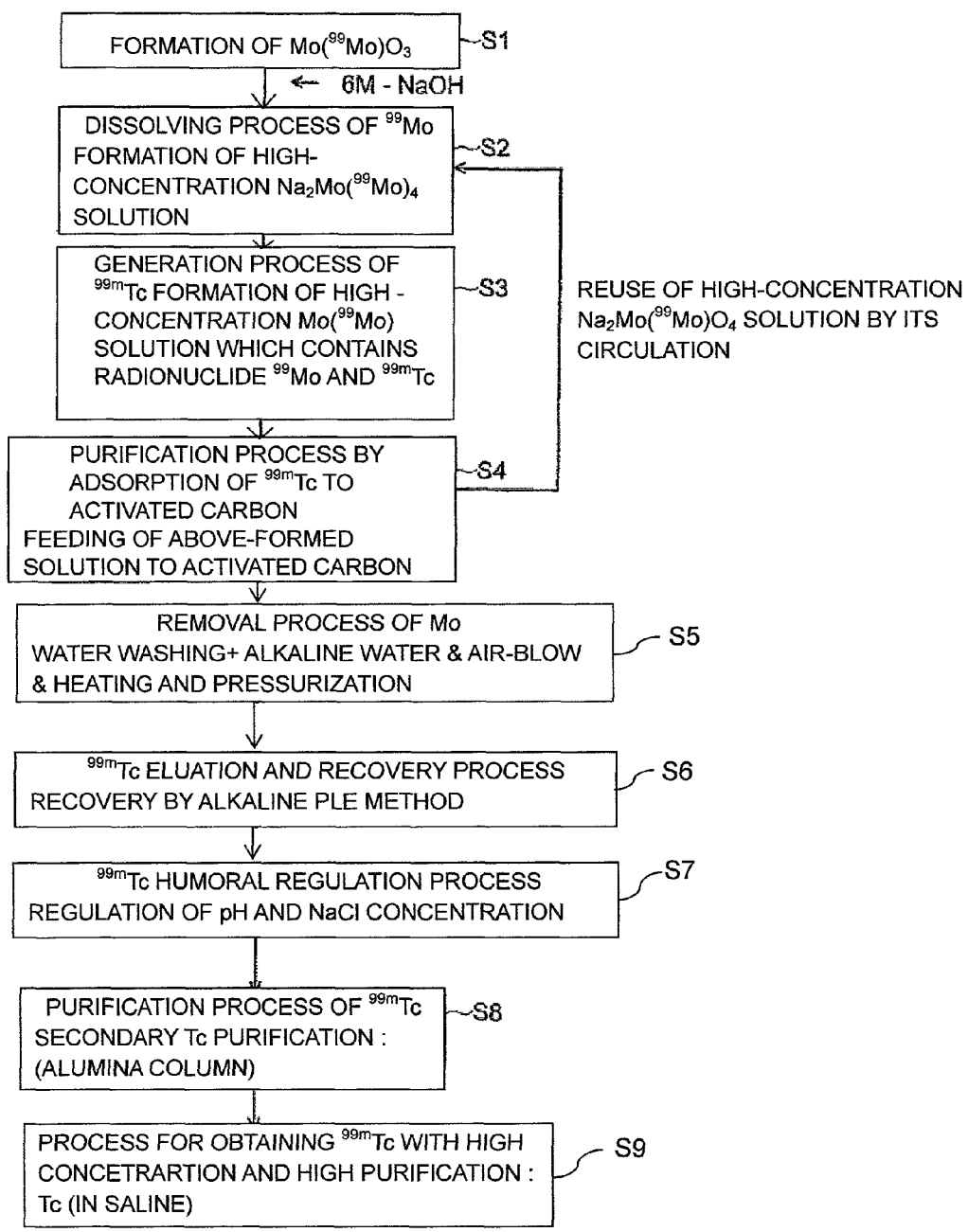
FIG. 3 illustrates the process of one embodiment of the present invention.

This example corresponds to the FIG. 3 shown later. On the occasion of generation, the Mo solution containing radioactive $^{99}$Mo means a high concentration Mo solution which contains 500 g of Mo in 2 L of the Mo solution, for example. Hereinafter, this solution is called the high concentration Mo solution. Here, the high concentration means the concentration for the high concentration Mo solution containing 500 g of Mo in above-mentioned 2 L to become necessary to obtain the requirement of $^{99m}$Tc, for example, to an extent of 500 i per once.

Plumbing pipes land 8 equipped with three-way valves 5 and 6 is provided for the bottom of Mo container (1) 2 and Mo container (2) 3, respectively. Moreover, Mo container (1) 2 and Mo container (2) 3 are connected to the bottom of the control tank 4 through three-way valves 5 and 6 and plumbing pipes 7 and 8, and moreover the other plumbing pipes 9 and 10. The termination of plumbing pipes 7 and 8 is equipped with a three-way valve 13. The control tank 4 has a function of the level adjustment mechanism. The bottom of control tank 4 is connected to the one end (the top face in FIG. 1) of the Tc enrichment, purification and recovery-system 16 through a three-way valve 15 which is set up in a plumbing pipe 14. This Tc enrichment, purification and recovery-system is equipped with the absorption column which has the activated carbon.

A plumbing pipe 17 and a three-way valve 18 set up therein, are prepared for the other edge (the lower edge in FIG. 1) of the Tc enrichment, purification and recovery-system 16, and connected to the three way valve 13 which is set up in the termination of plumbing pipes 7 and 8. $^{99m}$Tc is generated as the daughter nuclide of $^{99}$Mo in the high concentration Mo solution of Mo container (1) 2 and Mo container (2) 3, and the high concentration Mo solution which contains radionuclides $^{99}$Mo and $^{99m}$Tc is formed. The new high concentration Mo solution which contains $^{99}$Mo is alternately replaced and supplied to either Mo container (1) 2 or Mo container (2) 3, for example every two weeks.

Although technetium-99 ($^{99m}$Tc) emitting γ-ray (radiation) with weak energy is used for a medical diagnosis like SPECT, the amount of radioactivity of technetium-99 ($^{99m}$Tc) decreases to ¹⁄₁₆ in one day due to its half-life of 6 hours. To compensate for this, $^{99}$Mo which is the parent radionuclide of $^{99m}$Tc is kept, and $^{99m}$Tc generated by occurrence of beta-minus decay of $^{99}$Mo is separated and utilized. Thus, the way of obtaining the daughter nuclide using the radiation-equilibrium relation between the parent-nuclide and the daughter nuclide is called the milking method.

Here, the method of obtaining the daughter nuclide using the radioactive equilibrium relationship between the mother-nuclide and the daughter nuclide is designated the milking. Also, to perform the milking is named the milking treatment, and the solution which contains the daughter nuclide is named the milking solution. Accordingly, the high concentration Mo solution which contains $^{99}$Mo here means the solution which contains $^{99}$Mo used to obtain the requirement of $^{99m}$Tc by utilizing the radioactive equilibrium relationship, as mentioned above.

The high concentration Mo($^{99}$Mo) solution is introduced into the Tc purification and recovery system 16 by adsorption, which has an activated carbon column from the lower part of the Tc purification and recovery system 16 through plumbing pipe 7 and plumbing pipe 8, three-way valve 13, and plumbing pipe 17. Because Tc purification and recovery system 16 is equipped with the adsorption column which has the activated carbon, $^{99m}$Tc can be adsorbed selectively by feeding the high concentration Mo($^{99}$Mo) solution which contains the requirement of $^{99m}$Tc in this activated carbon. The purification and enrichment of $^{99m}$Tc are accomplished in this process. Here, relations of $^{99}$Mo amount and $^{99m}$Tc amount to Mo amount (being 500 g here) in the high concentration Mo solution are indicated as follows:

The half-life of $^{99}$Mo.65.94 h, The half-life of $^{99m}$Tc: 6.01 h

The $^{99}$Mo quantity in 500 Ci=1.04 mg (1/500,000 to 500 g of Mo).

The $^{99m}$Tc quantity in 500 Ci=0.095 mg (1/5,000,000 to 500 g of Mo).

$^{99}$Mo in case of $5 \times 10^4$ Bq or less, the $^{99}$Mo amount is $6 \times 10^{15}$ or less to 500 g of Mo.

$^{99m}$Tc in case of $6 \times 10^4$ Bq or less, the $^{99m}$Mc amount is $6 \times 10^{-16}$ or less to 500 g of Mo.

Thus, $^{99m}$Tc can be adsorbed by the activated carbon, even when there exists only a little amount of $^{99m}$Tc in the high concentration Mo solution.

A large amount of Mo containing $^{99}$Mo which is not adsorbed in the Tc enrichment, purification and recovery-system 16, are returned to the control tank 4 through the three-way valve 15 and the plumbing pipe 14, and further to either Mo container (1) 2 or Mo container (2) 3. In this way, using the Mo solution which is contained in either of two Mo containers, $^{99m}$Tc adsorption treatment is undergone every 24 hours everyday for total about 2 weeks and the Mo solution that $^{99m}$Tc is recovered is returned to the original Mo container (either of Mo container (1) 2 and (2) 3). After this process, $^{99m}$Tc which is enriched, purified and recovered in Tc enrichment, purification and the recovery-system 16 is transferred to the desorption process.

Thus, the high concentration Mo solution which contains $^{99}$Mo, is formed as the high solution Mo solution which contains radionuclide $^{99}$Mo by directly dissolving the Mo compound (MoO$_3$) irradiated with neutron in a nuclear reactor with an alkaline solution, and supplied to a plurality of Mo containers. Tc is adsorbed and enriched by alternately feeding the high concentration Mo($^{99}$Mo) solution stored in these plural Mo containers to the adsorption column which has the above-mentioned activated carbon, and then the Tc elution, purification and recovery is accomplished.

Feed system 22 is connected to a three-way valve 18 through a plumbing pipe 20 and a three-way valve 21. The washing solution, the Tc eluent and the others for desorption of Mo($^{99}$Mo), which remains in Tc enrichment purification and recovery-system 16 (the activated carbon column), are distributed from this feed system 22, and introduced to the Tc enrichment purification and recovery-system 16.

First, in the desorption process, Mo($^{99}$Mo) is desorbed by introducing the $^{99}$Mo desorbent from the feed system 22, and this solution is thrown as $^{99}$Mo washing waste fluid to a liquid waste tank 32. Then, Mo($^{99}$Mo) desorption process is stopped and transferred to Tc desorption process in which the Tc desorbent is introduced from the feed system 22 and Tc adsorbed to the activated carbon is desorbed.

Tc enrichment, purification and recovery-system 16 is connected to humoral regulation system 25 through the three-way valve 15, and further through a plumbing pipe 23 and a three-way valve 24 set up therein. Desorbed Tc is introduced into the humoral regulation system 25 together with the desorbent. The humoral regulation is carried out by adding a reagent for humoral regulation 34 in this humoral regulation system, and is connected to second purification system 27 through a plumbing pipe 26 and further with Tc recovery equipment 29 through a plumbing pipe 28.

This system 100 is equipped with waste fluid systems after using $^{99}$Mo 30 and 31 and washing waste fluid system 32, and each system is properly regulated by control system 33, as shown in FIG. 1.

Figure 2:
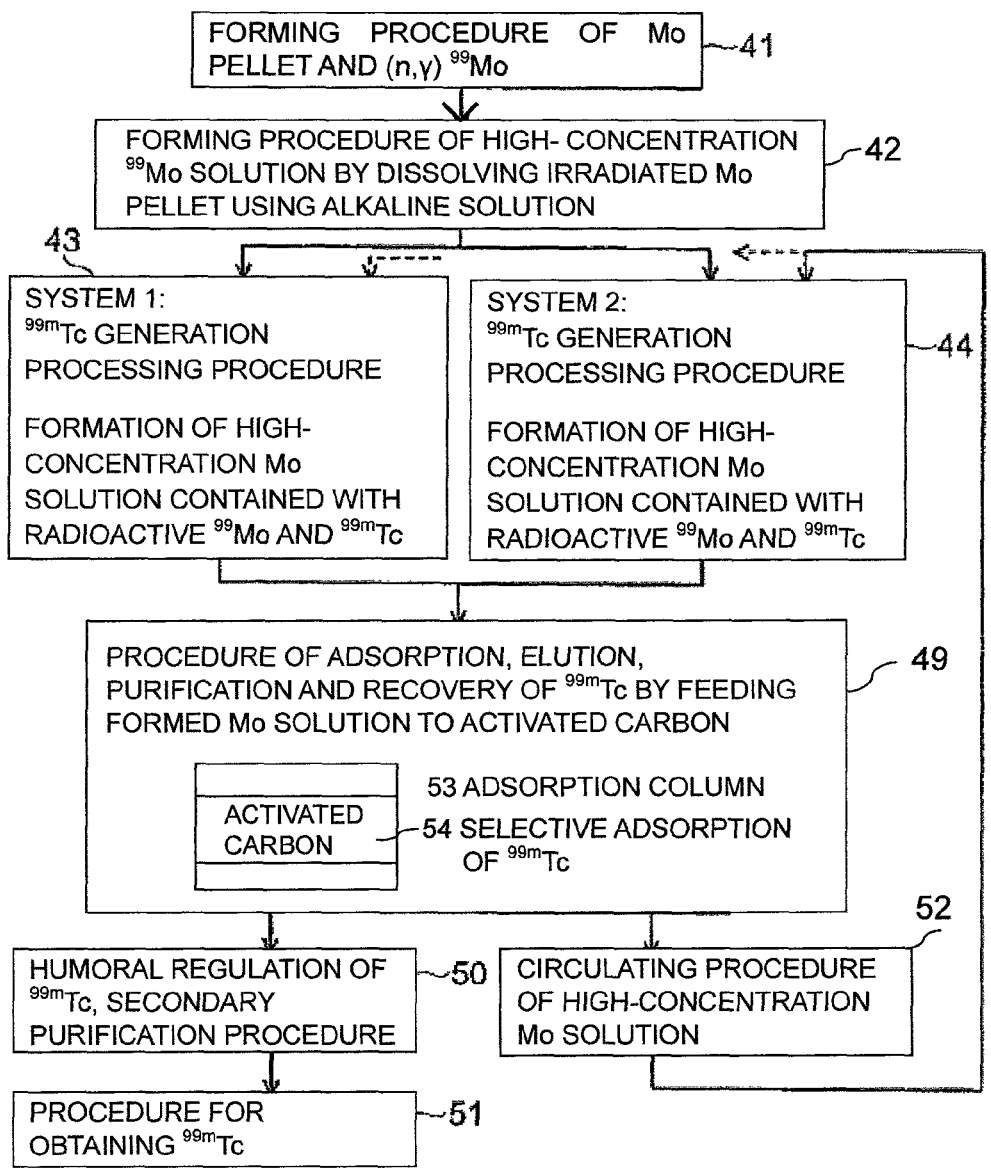
FIG. 2 illustrates the processing procedures and method of one embodiment of the present invention.

FIG. 2 illustrates the method and the process for purifying and recovering Tc by the treatments using this modal system which is illustrated in FIG. 1. In FIG. 2, the system for highly enriching, purifying and separating, and eluting and recovering 99mTc of this embodiment, comprises forming procedure of (n,γ)$^{99}$Mo 41, forming procedure of high concentration Mo($^{99}$Mo) solution 42, Tc generation processing procedures 43 and 44, procedure of adsorption, elution, purification and recovery of $^{99m}$Tc 49, secondary purification procedure for humoral regulation of $^{99m}$TC 50, procedure for obtaining $^{99m}$Tc 51 and recirculating procedure of high concentration Mo solution 52.

$^{99}$Mo is necessary to utilize $^{99m}$Tc. To produce $^{99}$Mo in large quantity, (n,γ)$^{99}$Mo is formed using the forming procedure of Mo pellet by the (n,γ) method in which natural Mo is irradiated in the nuclear reactor. In this embodiment, for example, a pellet formed by the (n,γ) method is used. Mo may be a powder. The Mo pellet which generates $^{99}$Mo in this way, is directly dissolved with an alkaline solution by introducing the alkaline solution using the forming procedure of the high concentration Mo solution. The alkaline can use NaOH. Tc is generated using Tc generation processing procedures 43 and 44. In generation of this Tc, system 1 (43) and system 2 (44) are used. These systems (1) and system (2), respectively, correspond to Mo container (1) 2 and Mo container (2) 3 in FIG. 1.

The high concentration Na$_2$Mo($^{99}$Mo)O$_4$ solution is formed when dissolving the Mo pellet irradiated with neutron in the nuclear reactor with a NaOH solution. The high concentration Mo($^{99}$Mo) solution which contains radionuclides $^{99}$Mo and $^{99m}$Tc, is formed by generating $^{99m}$Tc as the daughter nuclide of $^{99}$Mo using the high concentration $^{99}$Mo solution. Thus, according to this method, the Na$_2$Mo($^{99}$Mo)O$_4$ solution obtained by dissolving MoO$_3$ target irradiated in the nuclear reactor with the alkaline (NaOH) solution is alternately put into either of system 1 and system 2 once every week (last week and this week, respectively). Then, either of both Mo($^{99}$Mo) solutions is alternately introduced into the procedure of adsorption, elution, purification and recovery procedure of $^{99m}$Tc 49 which composes Tc purification and recovery-system by adsorption 16 (FIG. 1), and fed to Tc adsorption column 53.

The adsorption column 53 has activated carbon 54. $^{99m}$Tc adsorption procedure is composed of the Tc adsorption column 53 which has activated carbon 54. $^{99m}$Tc in high concentration Na$_2$Mo($^{99}$Mo)O$_4$ solution of either of systems 1 and 2 or the both is adsorbed by feeding the high concentration Na$_2$Mo($^{99}$Mo)O$_4$ solution to activated carbon 54 in this way. The activated carbon 54 adsorbs $^{99m}$Tc selectively. The amount of adsorbed $^{99m}$Tc increases along with alternate adsorptions of a small amount of $^{99m}$Tc in this way. $^{99m}$Tc concentration can be enriched to, for example, 40 times and more, compared with 99mTc concentration in the high concentration Na$_2$Mo($^{99}$Mo)O$_4$ solution by combining this activated carbon adsorption method with latter desorption method. This enables $^{99m}$Tc to be enriched to the proper concentration as the raw material for the radioactive medicine. Incidentally, according to the present invention, $^{99m}$Tc can be enriched in an optional enrichment factor.

In this embodiment, the high concentration alkaline solution is used as a Tc desorbent used for desorption of Tc which is adsorbed to activated carbon 54. Next, $^{99m}$TC is recovered by desorption treatment of $^{99m}$Tc with the desorbent by $^{99m}$Tc recovery procedure from the activated carbon to which $^{99m}$Tc is adsorbed. The absorption, desorption by elution and purification, and purification and recovery of $^{99m}$Tc are performed by these procedures.

The high concentration $Na_2Mo(^{99}Mo)O_4$ solution in which $^{99m}Tc$ is adsorbed and recovered, is returned to system 1 or system 2 by the circulation means of high concentration $Mo(^{99}Mo)$ solution 52, and recovered and reused as the high concentration $Na_2Mo(^{99}Mo)O_4$ solution.

A part of $Mo(^{99}Mo)$ which is adsorbed to the activated carbon, is removed from the activated carbon by the $Mo(^{99}Mo)$ washing process.

The secondary purification of the recovered Tc is made by removing the remained $^{99}Mo$ by the alumina column method after $^{99m}Tc$ humoral generation by the secondary purification procedure of 99mTc humoral regulation, and $^{99m}Tc$ is collected and recovered by the procedure for obtaining $^{99m}Tc$ 51.

As above-mentioned, the high concentration Mo solution is circulated to systems 1 and 2 by the circulation means of high Mo solution 52 to reuse the high concentration $Mo(^{99}Mo)$ solution after 99mTc adsorption. That is, high concentration $Mo(^{99}Mo)$ solution is returned to system 1 or system 2 and is reused, and then $^{99m}Tc$ is newly generated by $^{99m}Tc$ generation processing in these systems. Thus, the high concentration $Mo(^{99}Mo)$ solution is circulated and reused.

In this way, the system for highly enriching, purifying and separating, and eluting and recovering $^{99m}Tc$, and the recovery method are established as the 99Mo solution-type Tc master milker for using of the high concentration $Mo(^{99}Mo)$ solution, which enables to obtain an enriched $^{99m}Tc$ solution based on the physiological saline. This solution is used for medical diagnosis as the raw material of the radioactive medicine.

FIG. 3 illustrates a process of highly enriching, purifying and separating, and eluting and recovering $^{99m}Tc$.

In FIG. 3 this process comprises formation of $Mo(^{99}Mo)O_3$ S1, a dissolving process of $Mo(^{99}Mo)$ S2, a generation process of $^{99m}Tc$ formation S3, a purification process by adsorption of $^{99m}Tc$ to activated carbon S4, a removal process of Mo by water and weak alkaline of 0.01 mole of NaOH S5, a $^{99m}Tc$ elution and recovery process S6, $^{99m}Tc$ humoral regulation process S7, purification process of $^{99m}Tc$ for recovering and purifying $^{99m}Tc$ by washing and removing the remained $Mo(^{99}Mo)$ using the alumina column method S8, and a process for obtaining $^{99m}Tc$ with high concentration and high purification S9.

The whole operation is as follows:
(1) dissolving of the irradiated $Mo(^{99}Mo)_3$ pellet→(2) formation of $Na_2Mo(^{99}MO)O_4$ solution→(3) Tc adsorption and recovery (total recovery of the high concentration Mo solution used as an undiluted solution of $^{99}Mo$ for Tc adsorption and recovery (returning to the original tank and reusing 24 hours later))→(4) washing and removal of $Mo(^{99}Mo)$ which adheres to and remains in activated carbon→(5) Tc elution, purification and recovery→(6) regulation of pH and NaCl concentration of Tc recovered solution→(7) Tc secondary purification by the alumina column method (final purification)→(8) collection of Tc recovered solution (Tc≥1 Ci/mL, a physiological saline base, the neutral pH, containing no $^{99}Mo$).

The present invention is composed of the eight processes mentioned above.

As the elution and recovery method of $^{99m}Tc$ adsorbed to the activated carbon after high enrichment and adsorption of $^{99m}Tc$ in the high concentration $^{99m}Tc$ solution using the activated carbon, the remained $Mo(^{99}Mo)$ is removed by washing the activated carbon with a dilute alkaline solution, and further $^{99m}Tc$ in the high concentration $Mo(^{99}Mo)$ solution can be highly enriched, purified and separated, and eluted and recovered by efficiently eluting, purifying and recovering $^{99m}Tc$ by treatment with a high concentration alkaline solution.

As the elution and recovery method of $^{99m}Tc$ adsorbed to the activated carbon after high enrichment and adsorption of $^{99m}Tc$ in the high concentration $^{99m}Tc$ solution using the activated carbon, the remained $Mo(^{99}Mo)$ is removed by washing the activated carbon with a dilute alkaline solution. Furthermore, as the efficient elution and recovery method of $^{99m}Tc$ by treatment of $^{99m}Tc$ with the high concentration alkaline solution, $^{99m}Tc$ in the high concentration $Mo(^{99}Mo)$ solution can be highly enriched, purified and separated, and eluted and recovered by treating the activated carbon with NaOH solution of 0.05 mole and more at 100° C. and more and at 10 atoms and more to improve the elution and recovery rate of 99mTc.

As the elution and recovery method of $^{99m}Tc$ adsorbed to the activated carbon after high enrichment and adsorption of $^{99m}Tc$ in the high concentration 99mTc solution using the activated carbon, the high enrichment, purification and separation, and elution and recovery of $^{99m}Tc$ in the high concentration Mo ($^{99}Mo$) solution can be performed selectively by eluting and recovering $^{99m}Tc$ electrochemically using the activated carbon as a cathode.

As the elution and recovery method of $^{99m}Tc$ adsorbed to the activated carbon after the high enrichment and adsorption of $^{99m}Tc$ in the high concentration $^{99m}Tc$ solution using the activated carbon, $^{99m}Tc$ adsorbed to the activated carbon can be eluted and recovered without heating or pressurization by using a hydrazine or thiocyanic acid solution as a reducer of $^{99m}Tc$ elute, which facilitates the elusion and recovery of $^{99m}Tc$.

Incidentally, the Tc milking time is 4 hours per batch in a whole process, and $^{99m}Tc$ can be recovered at Tc concentration of 1 Ci/mL or more in the physiological saline of about 100 to 150 mL.

FIG. 4 to FIG. 9 shows experimental results.

Figure 4:
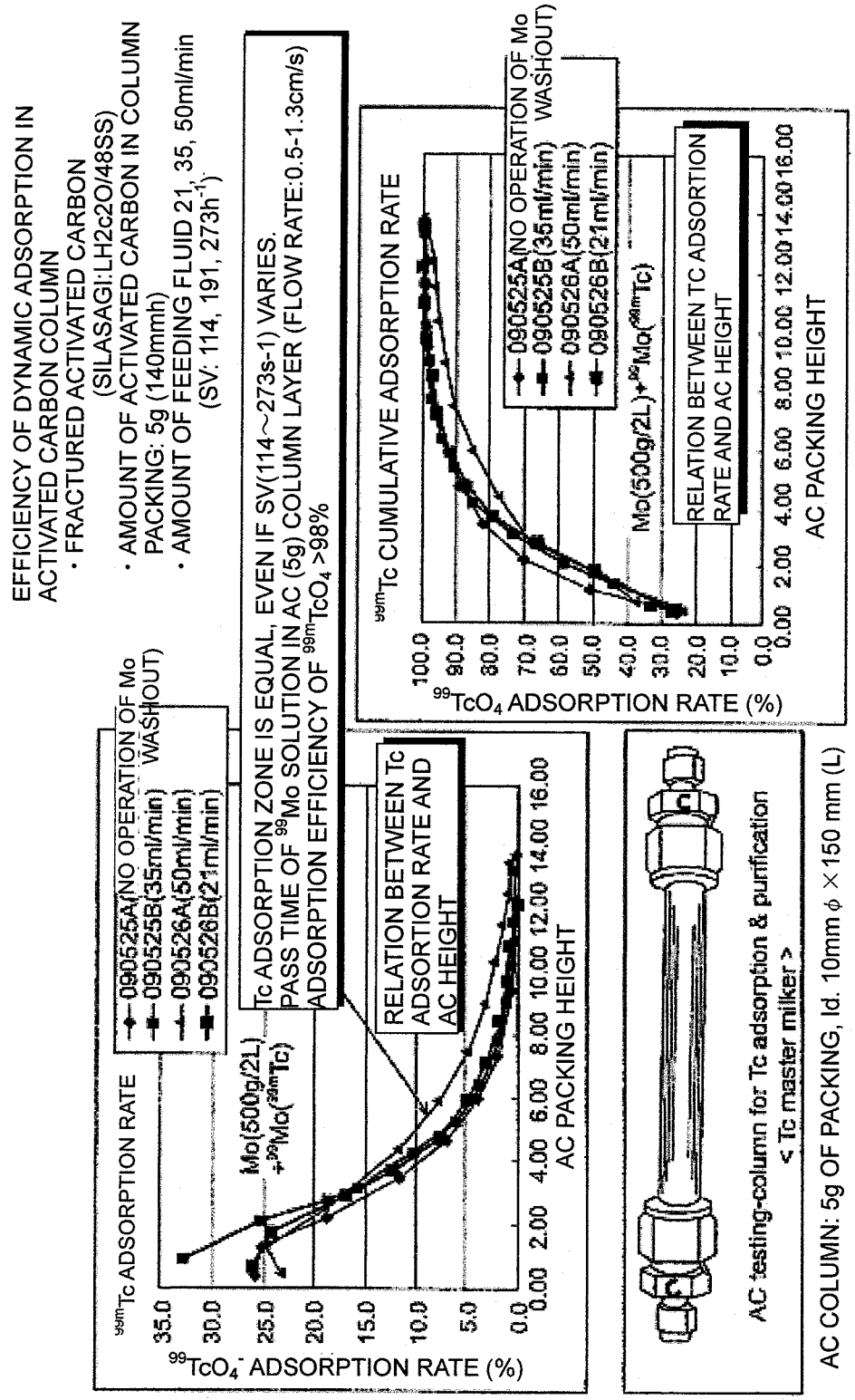
FIG. 4 shows Tc dynamic adsorption efficiency of the AC (activated carbon) absorption column.

FIG. 4 shows Tc dynamic adsorption efficiency of AC absorption column. As indicated in the figure, Tc adsorption zone is equal even if SV (the sky pipe speed: 114 to 273 h-1) varies. The pass time of $^{99}Mo$ solution in the column layer of AC (5 g) is 4.4 to 11 seconds (the current velocity: 0.5 to 1.3 cm/s) and $^{99m}Tc$ in high concentration Mo solution is adsorbed and recovered in the efficiency of 98% and more.

Figure 5:
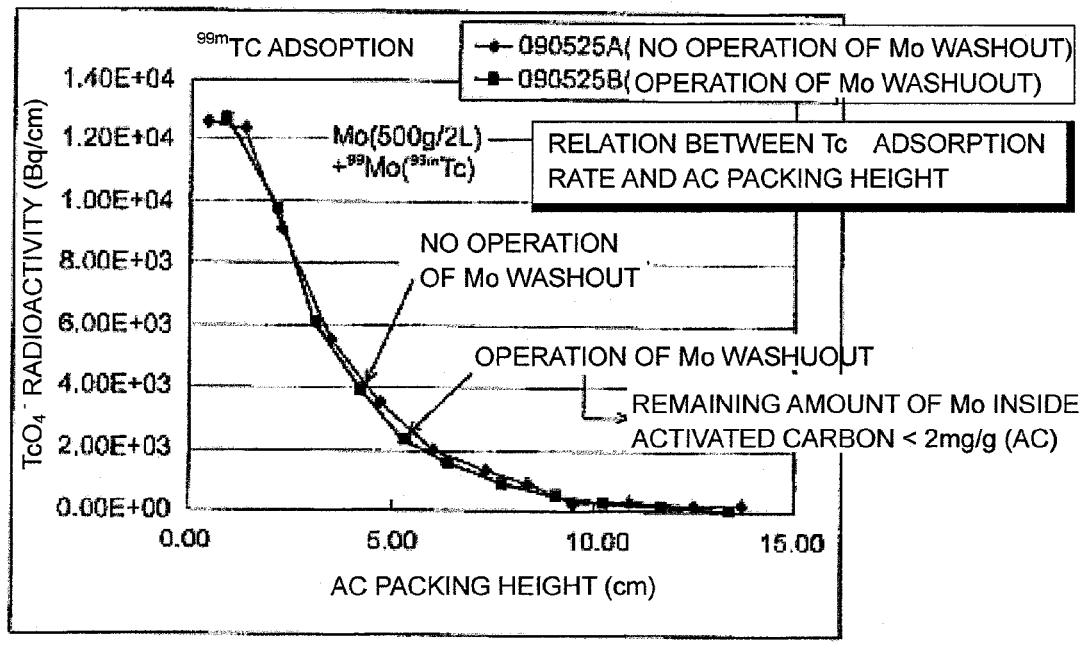
FIG. 5 shows the operation efficiency of Mo washout in Tc absorption column.

FIG. 5 shows Mo washout efficiency in Tc adsorption column 16. From this figure it is found that there is no movement of Tc adsorption zone even when the operation of Mo washout is undergone. Once $^{99m}Tc$ is adsorbed to the activated carbon, $^{99m}Tc$ stays behind it without removal even in washing and removal processing of remained $Mo(^{99}Mo)$ therein.

Figure 6:
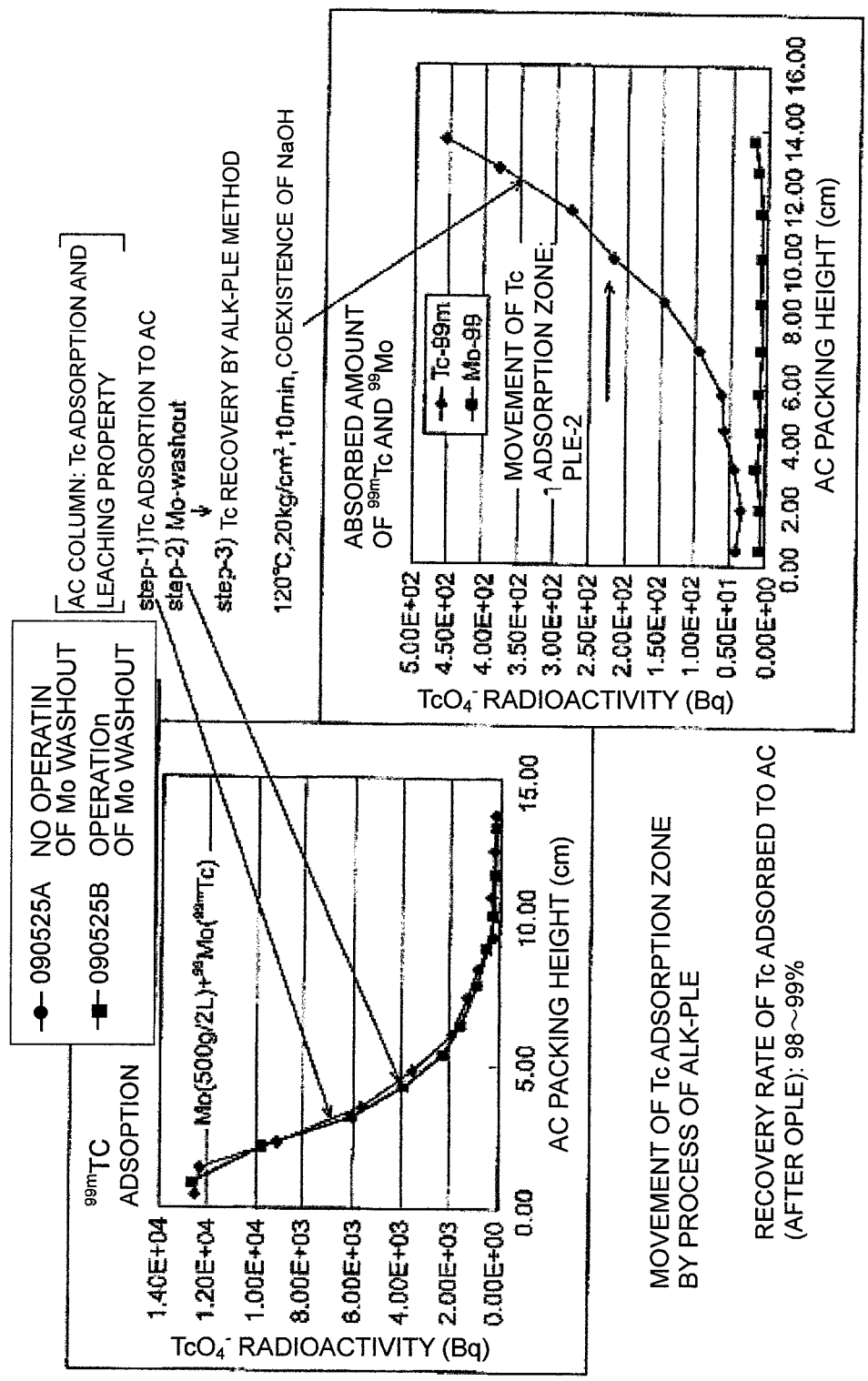
FIG. 6 shows the alk-PLE efficiency in Tc recovery from the Tc absorption column.

FIG. 6 shows the elution efficiency of $^{99m}Tc$ in extraction processing of the alkaline pressurized solution (alk-PLE) which is performed as the Tc recovery operation from Tc adsorption column. From this figure, the movement of the $^{99m}Tc$ adsorption zone is found, wherein $^{99m}Tc$ is adsorbed to the activated carbon column by the alk-PLE processing. The recovery rate of Tc adsorbed to AC by this alk-PLE processing is 98 to 99%.

Figure 7:
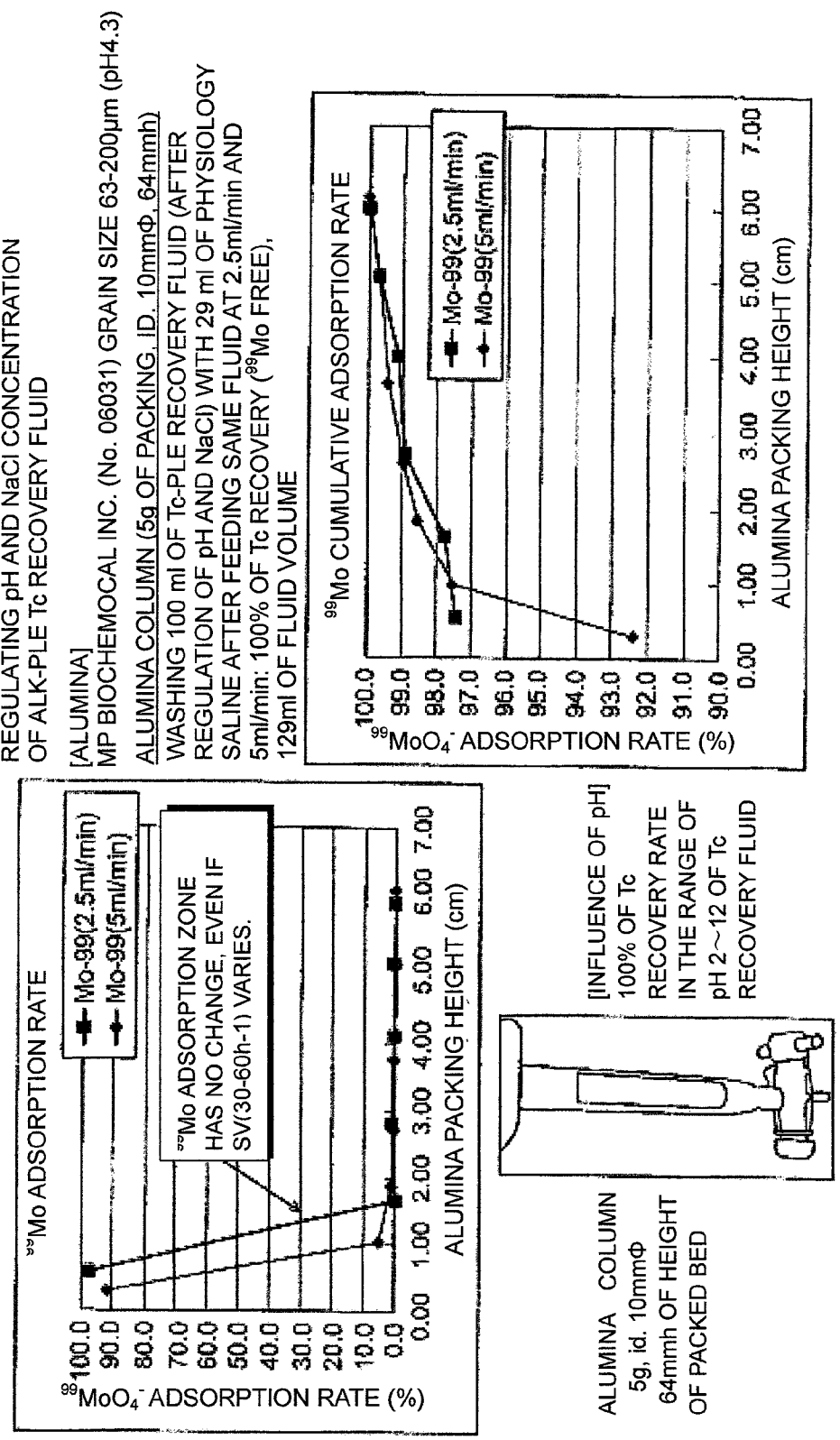
FIG. 7 shows the $^{99}$Mo dynamic adsorption efficiency in the purification and recovery of $^{99m}$Tc as the evaluated result of an alumina column performance.

FIG. 7 shows $^{99}Mo$ dynamic adsorption efficiency in the purification and recovery of $^{99m}Tc$ as the evaluated result of an alumina column performance. From this figure, even if SV (30 to 60 h-1) varies, $^{99m}Tc$ can be eluted, purified and recovered in a 100% yield in a trapped state of $^{99}Mo$ inside the alumina column due to no change of $^{99}Mo$ adsorption zone, which causes $^{99m}Tc$ to be obtained with high purity.

FIG. 8 shows $^{99m}$Tc yield in alumina column separation. The purification and recovery rate of Tc by the alumina column is 100%.

Figure 9:
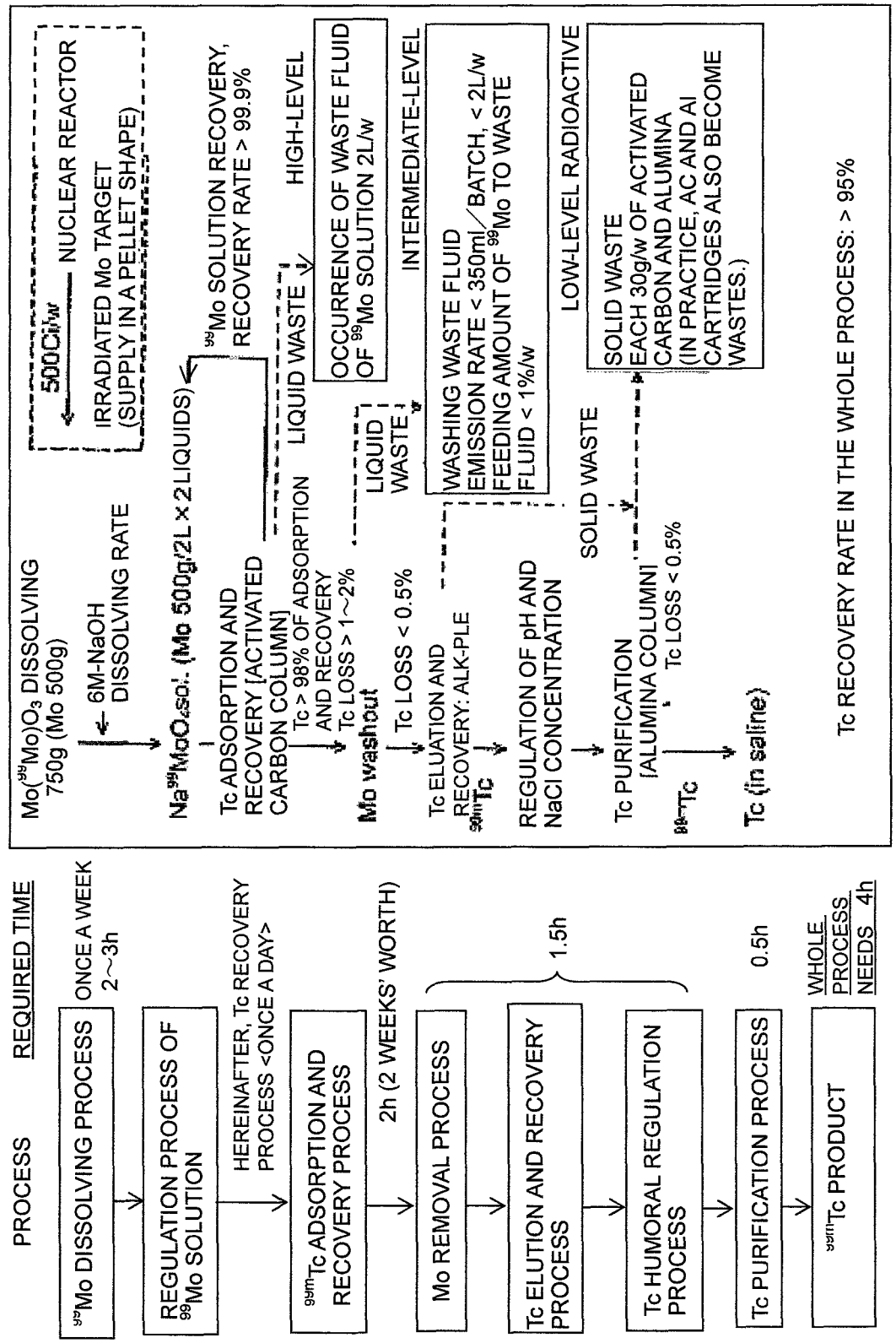
FIG. 9 shows the required process time, the material balance, and the amount of occurred waste by $^{99m}$Tc collection process with $^{99}$Mo 500 i scale ($^{99m}$Tc master milker process).

FIG. 9 shows the material balance in $^{99m}$Tc collection process with $^{99}$Mo 500 Ci scale.

Since in this system used as the $^{99}$Mo solution-type Tc master milker, no use of a solid-like or gelatinous $^{99}$Mo adsorption support prevents any constituent elements of an adsorbent (Zr, for example) to be elusidated and mixed by the radiation damage of the $^{99}$Mo adsorption support and moreover $^{99m}$Tc is in a dissolved state in $^{99}$Mo solution, the concerns to the $^{99m}$Tc milking efficiency derived from the $^{99}$Mo absorption support are unnecessary. The activated carbon used in this system can selectively adsorb $^{99m}$Tc with high efficiency without adsorption of $^{99}$Mo in the high concentration Mo solution. Furthermore, $^{99m}$Tc can be applied in the best condition to the raw material for the radioactive medicine by using the $^{99m}$Tc solution based on the physiological saline, in which Tc adsorbed to the activated carbon is eluted. Also, in the highly enriching, purifying and separating, and eluting and recovering process of a very small amount of $^{99m}$Tc from the high concentration Mo($^{99}$Mo) solution, $^{99m}$Tc maintains the form of pertechnetic acid ($^{99m}$TcO$_4^-$) in all the processes, when recovering $^{99m}$Tc using the high concentration alkaline from the activated carbon to which $^{99m}$Tc is adsorbed. Incidentally, in $^{98}$Mo(n, γ) reaction of MoO$_3$, $^{92}$Mo, $^{95}$Mo and $^{96}$Mo of Mo isotopes which are contained in MoO$_3$ of the neutron irradiation target for the $^{99}$Mo production, generates $^{92m}$Nb, $^{96}$Nb and $^{96}$Nb of radioactive niobiums by each (n, γ) reaction, respectively, but these radioactive niobiums are never adsorbed to the activated carbon when $^{99m}$Tc in the high concentration Mo($^{99}$Mo) solution is adsorbed and recovered using the activated carbon column. Therefore, these radioactive niobiums are never mixed into the $^{99m}$Tc recovery solution.

Since this system used as the $^{99}$Mo solution-type Tc master milker has several advantages of not only easy pharmaceutical affairs application and low cost due to no use of $^{99}$Mo adsorption support, but also reduction of the quantity of radioactive waste fluid or solid wastes which are generated in $^{99m}$Tc recovery. Furthermore, a very small amount of $^{99m}$Tc in the high concentration Mo($^{99}$Mo) solution can be purified and recovered in a high yield without contamination of $^{99}$Mo.

According to $^{99}$Mo solution method of this embodiment, The product of same $^{99m}$Tc ($^{99m}$Tc concentration and fluid volume) as one which is eluted and recovered by the present Fission-$^{99}$Mo alumina column method, can be steadily obtained from (n,γ)$^{99}$Mo solution. Thereby, the technology which can be used as $^{99m}$Tc master milker in production lines is established.

What is claimed is:

1. A method of recovering highly enriched $^{99m}$Tc as a raw material for a radioactive medicine, comprising the steps of:
    forming a high concentration Mo($^{99}$Mo) solution which contains radionuclides $^{99}$Mo and $^{99m}$Tc which is generated as the daughter nuclide of $^{99}$Mo, in formation of a high concentration Mo solution which contains radionuclide $^{99}$Mo as a raw material for a radioactive medicine;
    obtaining $^{99m}$Tc in said high-concentration Mo($^{99}$Mo) solution adsorbed to activated carbon selectively by feeding said formed high concentration Mo($^{99}$Mo) solution to an adsorption column which has said activated carbon, desorbing and removing Mo($^{99}$Mo) remaining in said activated carbon with a Mo desorbent, and recovering $^{99m}$Tc by desorption treatment of $^{99m}$Tc remaining in said activated carbon with a desorbent;
    making secondary purification to remove Mo($^{99}$Mo) remaining in said recovered $^{99m}$Tc by an alumina column-method; and
    re-forming a high concentration Mo($^{99}$Mo) solution which contains radionuclides $^{99}$Mo and $^{99m}$Tc by recirculating and recovering said high concentration Mo($^{99}$Mo) solution after said desorbing and removing of Mo($^{99}$Mo), and generating $^{99m}$Tc again in the re-formed high concentration Mo($^{99}$Mo) solution to a radiation-equilibrium state.

2. The method of recovering highly enriched $^{99m}$Tc according to claim 1, further comprising the steps of:
    forming said high concentration Mo solution which contains $^{99}$Mo by directly dissolving Mo compound irradiated with neutron in a nuclear reactor with an alkaline solution; supplying said high concentration Mo solution to a plurality of Mo containers; enriching $^{99m}$Tc with adsorption of the $^{99m}$Tc by feeding said high concentration Mo solution stored in said plurality of Mo containers to said adsorption column containing said activated carbon; and then eluting and purifying $^{99m}$Tc.

3. The method of recovering highly enriched $^{99m}$Tc according to claim 1, wherein
    the recovery of $^{99m}$Tc by said desorption treatment is performed by removing the residual Mo($^{99}$Mo) adhered to said activated carbon by washing said activated carbon for adsorbing $^{99m}$Tc with a relatively dilute alkaline solution, and further performing said desorption treatment of said activated carbon adsorbing $^{99m}$Tc with a relatively high concentration alkaline solution relative to the alkaline concentration of the dilute alkaline solution.

4. The method of recovering highly enriched $^{99m}$Tc according to claim 3, wherein
    $^{99m}$Tc is eluted and purified by treating said activated carbon with a NaOH solution of 0.05 mole (M) and more at 100° C. and more and at 5 atm and more.

5. The method of recovering highly enriched $^{99m}$Tc according to claim 1, wherein
    the recovery of $^{99m}$Tc by said desorption treatment is performed by an electrochemical treatment of said activated carbon adsorbing $^{99m}$Tc by using said activated carbon as a cathode.

6. A method for recovering highly enriched $^{99m}$Tc as a raw material for a radioactive-medicine, comprising the steps of:
    forming a high concentration Mo solution which contains radioactive $^{99m}$Tc as a raw material for a radioactive medicine;
    forming said high-concentration Mo solution which contains said radionuclides $^{99}$Mo and $^{99m}$Tc which is generated as the daughter nuclide of 99Mo;
    feeding said formed high-concentration Mo($^{99}$Mo) solution to an adsorption column which has activated carbon, obtaining $^{99m}$Tc in said high-concentration Mo($^{99}$Mo) solution adsorbed to said activated carbon selectively, and desorbing and removing Mo($^{99}$Mo) by washing Mo($^{99}$Mo) remaining in said activated carbon adsorbing $^{99m}$Tc with a Mo desorbent;
    adsorbing, desorbing, and recovering $^{99m}$Tc by desorption treatment of $^{99m}$Tc remaining in the activated carbon with a $^{99m}$Tc desorbent, after the desorbing and removing of Mo($^{99}$Mo) by washing Mo($^{99}$Mo) remaining in said activated carbon adsorbing $^{99m}$Tc with a Mo desorbent;
    removing Mo($^{99}$Mo) remaining in said recovered $^{99m}$Tc by an alumina column-method: and
    recirculating and recovering said high concentration Mo($^{99}$Mo) solution, generating $^{99m}$Tc again in the recirculated and recovered high concentration Mo($^{99}$Mo) solution to a radiation-equilibrium state, and re-forming a high concentration Mo solution containing radionuclides $^{99}$Mo and $^{99m}$Tc to reuse said high concentration Mo($^{99}$Mo) solution after said desorbing and removing of Mo($^{99}$Mo).

7. A method for recovering highly enriched $^{99m}$Tc as a raw material for a radioactive-medicine, comprising the steps of:

forming a high concentration Mo solution which contains radionuclide $^{99}$Mo as a raw material for a radioactive-medicine by directly dissolving a large amount of Mo with an alkaline solution;

forming said high concentration Mo solution which contains radionuclides $^{99}$Mo and $^{99m}$Tc which is generated to a radiation-equilibrium state so as to be the daughter nuclide of $^{99}$Mo;

obtaining $^{99m}$Tc in said high-concentration Mo($^{99}$Mo) solution adsorbed to activated carbon selectively by feeding said formed high concentration Mo($^{99}$Mo) solution to an adsorption column which has said activated carbon, and desorbing Mo($^{99}$Mo) by washing Mo($^{99}$Mo) remaining in said activated carbon with a Mo desorbent;

desorbing and recovering $^{99m}$Tc to recover $^{99m}$Tc by desorption treatment of $^{99m}$Tc with a $^{99m}$Tc desorbent from said activated carbon adsorbing $^{99m}$Tc;

removing Mo($^{99}$Mo) remaining in said recovered $^{99m}$Tc by an alumina column-method; and circulating and recovering said high-concentration Mo($^{99}$Mo) solution, generating $^{99m}$Tc again in the circulated and recovered high-concentration Mo($^{99}$Mo) solution to a radiation-equilibrium condition, and re-forming a high concentration Mo solution containing radionuclides $^{99}$Mo and $^{99m}$Tc to reuse said high concentration Mo($^{99}$Mo) solution after said desorbing of Mo($^{99}$Mo).

8. A method of recovering $^{99m}$Tc enriched to the required concentration as radioactive medicines and raw materials for its labeled compound, comprising the steps of:

forming a high concentration Na$_2$Mo($^{99}$Mo)O$_4$ solution of neutral pH in which a large amount of Mo($^{99}$Mo)O$_3$ is dissolved with NaOH, obtaining $^{99m}$Tc generated in the high concentration Na$_2$Mo($^{99}$Mo)O$_4$ solution adsorbed to activated carbon selectively, maintaining $^{99m}$Tc adsorbed to the activated carbon while desorbing the Mo($^{99}$Mo) from the activated carbon, and recovering at least a trace of the $^{99m}$Tc by desorption treatment of $^{99m}$Tc remaining in the activated carbon with a $^{99m}$Tc desorbent, and removing Mo($^{99}$Mo) remaining in said recovered $^{99m}$Tc by an alumina column-method.

* * * * *